United States Patent
Nomoto et al.

(10) Patent No.: US 9,549,922 B2
(45) Date of Patent: Jan. 24, 2017

(54) USE OF ERIBULIN AND LENVATINIB AS COMBINATION THERAPY FOR TREATMENT OF CANCER

(71) Applicant: Eisai R&D Management Co., Ltd., Tokyo (JP)

(72) Inventors: Kenichi Nomoto, Belmont, MA (US); Jiayi Wu, Brookline, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 18 days.

(21) Appl. No.: 14/315,930

(22) Filed: Jun. 26, 2014

(65) Prior Publication Data
US 2015/0005343 A1   Jan. 1, 2015

Related U.S. Application Data (60) Provisional application No. 61/839,542, filed on Jun. 26, 2013.

(51) Int. Cl.
*A61K 31/47* (2006.01)
*A61K 31/357* (2006.01)

(52) U.S. Cl.
CPC ............. *A61K 31/47* (2013.01); *A61K 31/357* (2013.01)

(58) Field of Classification Search
CPC ...... A61K 31/47; A61K 31/357; C07D 215/00
USPC .......................... 546/112, 153; 514/299, 311
See application file for complete search history.

(56) References Cited

U.S. PATENT DOCUMENTS

| | | |
|---|---|---|
| 6,214,865 B1 | 4/2001 | Littlefield et al. |
| 6,469,182 B1 | 10/2002 | Littlefield et al. |
| 6,653,341 B1 | 11/2003 | Littlefield et al. |
| 7,253,286 B2 | 8/2007 | Funahashi et al. |
| 7,470,720 B2 | 12/2008 | Littlefield et al. |
| 7,612,208 B2 | 11/2009 | Matsushima et al. |
| 7,982,060 B2 | 7/2011 | Austad et al. |
| 8,058,474 B2 | 11/2011 | Naito |
| 8,097,648 B2 | 1/2012 | Littlefield et al. |
| 8,772,269 B2 | 7/2014 | Owa et al. |
| 8,815,241 B2 | 8/2014 | Yamamoto |
| 8,937,056 B2 * | 1/2015 | Agoulnik et al. ............ 514/100 |
| 8,952,035 B2 | 2/2015 | Yamamoto |
| 8,962,650 B2 | 2/2015 | Narita et al. |
| 8,962,655 B2 | 2/2015 | Yamamoto |
| 8,969,344 B2 | 3/2015 | Matsui et al. |
| 9,006,240 B2 | 4/2015 | Uenaka et al. |
| 9,006,256 B2 | 4/2015 | Matsui |
| 9,012,458 B2 | 4/2015 | Nakagawa et al. |
| 2005/0119303 A1 | 6/2005 | Wakabayashi et al. |
| 2006/0135486 A1 | 6/2006 | Owa et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0239688 A1 | 9/2010 | Yamamoto |
| 2010/0324087 A1 | 12/2010 | Yamamoto |
| 2011/0293615 A1 | 12/2011 | Yamamoto |
| 2012/0077837 A1 | 3/2012 | Okamoto et al. |
| 2013/0123274 A1 | 5/2013 | Nakagawa et al. |
| 2014/0031384 A1 | 1/2014 | Narita et al. |

FOREIGN PATENT DOCUMENTS

| | | |
|---|---|---|
| CA | 2828946 A1 | 10/2012 |
| JP | 2016-8215 A | 1/2016 |
| WO | WO-99/65894 A1 | 12/1999 |
| WO | WO-2012/129100 A1 | 9/2012 |
| WO | WO-2012/144463 A1 | 10/2012 |
| WO | WO-2012/154935 A1 | 11/2012 |
| WO | WO-2012/166899 A2 | 12/2012 |
| WO | WO-2015/134399 A1 | 9/2015 |
| WO | WO-2015/183961 A1 | 12/2015 |
| WO | WO-2015/184145 A1 | 12/2015 |

OTHER PUBLICATIONS

International Search Report and Written Opinion for PCT/JP2014/067723, mailed Oct. 10, 2014 (9 pages).
Asano et al., "Broad-spectrum preclinical combination activity of eribulin combined with various anticancer agents in human breast cancer, lung cancer, and melanoma xenograft models," 26th EORTC-NCI-AACR Symposium on Molecular Targets and Cancer Therapeutics, Nov. 19, 2014, Barcelona, Spain. Abstract No. 46 (2 pages).

* cited by examiner

*Primary Examiner* — Golam M M Shameem
(74) *Attorney, Agent, or Firm* — Clark & Elbing LLP; Susan M. Michaud (57) ABSTRACT

The invention provides methods and compositions for use in treating diseases associated with excessive cellular proliferation, such as cancer.

25 Claims, 3 Drawing Sheets

USE OF ERIBULIN AND LENVATINIB AS COMBINATION THERAPY FOR TREATMENT OF CANCER

This application claims benefit of U.S. Ser. No. 61/839,542, filed Jun. 26, 2013, which is incorporated herein by reference.

BACKGROUND OF THE INVENTION

Cancer is a term used to describe a wide variety of diseases that are each characterized by the uncontrolled, malignant growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine the extent of metastasis, systemic approaches to therapy are usually undertaken when any evidence of spread is detected. These approaches involve the administration of, for example, chemotherapeutic drugs that interfere with the growth of rapidly dividing cells, such as cancer cells.

Halichondrin B is a structurally complex, macrocyclic compound that was originally isolated from the marine sponge *Halichondria okadai*, and subsequently was found in *Axinella* sp., *Phakellia carteri*, and *Lissodendoryx* sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, beta$^s$-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

Eribulin is a synthetic analog of halichondrin B. Eribulin is also known as ER-086526, and has been assigned CAS number 253128-41-5 and US NCI designation number NSC-707389. The mesylate salt of eribulin (eribulin mesylate, which is marketed under the trade name HALAVEN® and is also known as E7389) is approved for the treatment of patients with breast cancer who have previously received at least two chemotherapeutic regimens for the treatment of metastatic disease that should have included an anthracycline and a taxane in either the adjuvant or metastatic setting.

The chemical name for eribulin mesylate is (2R,3R,3aS,7R,8aS,9S,10aR,11S,12R,13aR,13bS,15S,18S,21S,24S,26R,28R,29aS)-2-[(2S)-3-amino-2-hydroxypropyl]hexacosahydro-3-methoxy-26-methyl-20,27-bis(methylene)-11,15:18,21:24,28-triepoxy-7,9-ethano-12,15-methano-9H,15H-furo[3,2-i]furo[2',3':5,6]pyrano[4,3-b][1,4]dioxacyclopentacosin-5(4H)-one, methanesulfonate (salt), and it can be depicted as:

E7080 (also known as lenvatinib mesylate) is an active inhibitor of multiple receptor tyrosine kinases (e.g., receptor tyrosine kinases involved in angiogenesis and tumor proliferation) including vascular endothelial growth factor (VEGF), fibroblast growth factor (FGF), platelet-derived growth factor receptor α (PDGFRα), KIT, and RET protooncogene receptors. It has been assigned CAS number 857890-39-2 (also see 417716-92-8). The chemical name for lenvatinib mesylate is 4-[3-chloro-4-[[(cyclopropylamino)carbonyl]amino]phenoxy]-7-methoxy-6-quinolinecarboxamide, methanesulfonate (1:1). [It is also named as 4-[3-chloro-4-(N'-cyclopropylureido)phenoxy]-7-methoxyquinoline-6-carboxamide, and N-{4-[(6-carbamoyl-7-methoxyquinolin-4-yl)oxy]-2-chlorophenyl}-N'-cyclopropylurea monomethanesulfonate.] Lenvatinib mesylate can be depicted as:

SUMMARY OF THE INVENTION

The invention is based on the observation that the combination of eribulin and lenvatinib shows improved (e.g., synergistic) antitumor effects. Therefore, the present invention features the co-administration of eribulin (or a pharmaceutically acceptable salt thereof, e.g., eribulin mesylate) and lenvatinib (or a pharmaceutically acceptable salt thereof, e.g., lenvatinib mesylate) in cancer treatment regimens, as well as the use of these agents for such treatment.

The invention thus provides methods for treating a subject (e.g., a human patient) having or at risk of developing cancer. The methods involve administering to a subject (i) eribulin or a pharmaceutically acceptable salt thereof (e.g., eribulin mesylate), and (ii) lenvatinib or a pharmaceutically acceptable salt thereof (e.g., lenvatinib mesylate). The invention also provides the use of these agents for the treatment of such a subject, as well as the use of these agents for the preparation of medicaments for the treatment of such a subject, as described herein. All descriptions of methods herein are applicable in the context of such uses.

The subject may be diagnosed with cancer, in treatment for cancer, or in post-therapy recovery from cancer. Further, the cancer may be a primary tumor, a metastasis, and/or a solid tumor. In various examples, the cancer can be selected from the group consisting of breast cancer, pancreatic cancer, lung cancer, colon cancer, rectal cancer, colorectal cancer, ovarian cancer, endometrial cancer, skin cancer (e.g., melanoma), prostate cancer, brain cancer, head and neck cancer, liver cancer, kidney cancer, bladder cancer, gastric cancer, gastrointestinal cancer, cancer of the blood (e.g., leukemia), cancer of the lymphatic system, thyroid cancer, bone cancer (e.g., osteosarcoma), and fibrosarcoma.

The eribulin or pharmaceutically acceptable salt thereof (e.g., eribulin mesylate) can be administered by intravenous infusion, for example, for about 1 to about 20 minutes, or for about 2 to about 5 minutes. Further, the eribulin or pharmaceutically acceptable salt thereof (e.g., eribulin mesylate) can be administered in an amount in the range of about 0.1 mg/m$^2$ to about 20 mg/m$^2$, or about 1.4 mg/m$^2$ or 1.1 mg/m$^2$. In addition, the eribulin or pharmaceutically acceptable salt thereof (e.g., eribulin mesylate) can be administered once on each of days 1 and 8 of a 21-day cycle.

The lenvatinib or pharmaceutically acceptable salt thereof (e.g., lenvatinib mesylate) can be administered orally, for example, in an amount in the range of about 0.1 mg to about 100 mg, or about 4 mg to about 24 mg. Further, in various examples, the lenvatinib or pharmaceutically acceptable salt thereof (e.g., lenvatinib mesylate) can be administered daily.

The eribulin or pharmaceutically acceptable salt thereof (e.g., eribulin mesylate), and the lenvatinib or pharmaceutically acceptable salt thereof (e.g., lenvatinib mesylate) can be administered substantially simultaneously or sequentially.

Treatment according to the methods of the invention can: (i) reduce the number of cancer cells; (ii) reduce tumor volume; (iii) increase tumor regression rate; (iv) reduce or slow cancer cell infiltration into peripheral organs; (v) reduce or slow tumor metastasis; (vi) reduce or inhibit tumor growth; (vii) prevent or delay occurrence and/or recurrence of the cancer and/or extend disease- or tumor-free survival time; (viii) increase overall survival time; (ix) reduce the frequency of treatment; and/or (x) relieve one or more of symptoms associated with the cancer.

The invention also includes methods for decreasing the size of a tumor in a subject. These methods involve administering to a subject (i) eribulin or a pharmaceutically acceptable salt thereof (e.g., eribulin mesylate), and (ii) lenvatinib or a pharmaceutically acceptable salt thereof (e.g., lenvatinib mesylate). In addition, the invention includes the use of these agents for decreasing the size of a tumor in a subject, as described herein.

Further, the invention includes kits for use in treating cancer, decreasing tumor size, or inducing or increasing an immune response to a tumor in a subject. The kits include (i) eribulin or a pharmaceutically acceptable salt thereof (e.g., eribulin mesylate), and (ii) lenvatinib or a pharmaceutically acceptable salt thereof (e.g., lenvatinib mesylate). Optionally, these agents are present in dosage form.

Other features of the invention will be apparent from the following detailed description, the drawings, and the claims.

DETAILED DESCRIPTION OF THE INVENTION

The invention provides methods for treating cancer involving administration of eribulin and lenvatinib (or pharmaceutically acceptable salts thereof, e.g., mesylate salt), as well as the use of these agents for cancer treatment or the preparation of medicaments therefor. As shown in the Examples section, below, eribulin mesylate and lenvatinib mesylate, when used in combination, potentiate the anti-cancer effects of one another. In one example, the combination therapy results in tumor regression. Accordingly, treatment of cancer by administering eribulin and lenvatinib (or pharmaceutically acceptable salts thereof, e.g., mesylate salt), according to the methods of the invention, can (i) reduce the number of cancer cells; (ii) reduce tumor volume; (iii) increase tumor regression rate; (iv) reduce or slow cancer cell infiltration into peripheral organs; (v) reduce or slow tumor metastasis; (vi) reduce or inhibit tumor growth; (vii) prevent or delay occurrence and/or recurrence of the cancer and/or extend disease or tumor-free survival time; (viii) increase overall survival time; (ix) reduce the frequency of treatment; and/or (x) relieve one or more of symptoms associated with cancer.

Pharmaceutical Compositions, Dosage, and Methods

Methods for the synthesis of eribulin (and pharmaceutically acceptable salts thereof, such as eribulin mesylate) are described, for example, in U.S. Pat. No. 6,214,865; U.S. Pat. No. 7,982,060; U.S. Pat. No. 8,350,067; and U.S. Pat. No. 8,093,410, each of which is incorporated herein by reference. Methods relating to lenvatinib (and pharmaceutically acceptable salts thereof, such as lenvatinib mesylate) and its synthesis are described, for example, in U.S. Pat. No. 7,612,092, which is incorporated herein by reference.

As noted above, eribulin and/or lenvatinib can optionally be used in the present invention in a salt form. There are no particular limitations as to the salt used, whether inorganic acid salt or organic acid salt. For example, the salt may be selected from methansulfonic acid salt (e.g., eribulin mesylate or lenvatinib mesylate), hydrochloric acid salt, sulfuric acid salt, citric acid salt, hydrobromic acid salt, hydroiodine acid salt, nitric acid salt, bisulfate, phosphoric acid salt, super phosphoric acid salt, isonicotinic acid salt, acetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, ethanesulfonic acid salt, benzenesulfonic acid salt, p-toluenesulfonic acid salt, pamoic acid salt (pamoate), and so on.

Pharmaceutical compositions including eribulin or lenvatinib (or pharmaceutically acceptable salts thereof, such as mesylate salt) can be prepared using standard methods known in the art (see, e.g., the patents noted above). Pharmaceutical compositions used in the invention can be prepared by, for example, mixing or dissolving the active ingredient(s), having the desired degree of purity, in a physiologically acceptable diluent, carrier, excipient, or stabilizer (see, e.g., Remington's Pharmaceutical Sciences (20$^{th}$ edition), ed. A. Gennaro, 2000, Lippincott, Williams & Wilkins, Philadelphia, Pa.). Acceptable diluents include water and saline, optionally including buffers such as phosphate, citrate, or other organic acids; antioxidants including butylated hydroxytoluene (BHT), butylated hydroxyanisole (BHA), ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine, or lysine; monosaccharides, disaccharides, or other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, the formulations of the invention contain a pharmaceutically acceptable preservative. In some embodiments the preservative concentration ranges from 0.1 to 2.0%, typically v/v. Suitable preservatives include those known in the pharmaceutical arts, such as benzyl alcohol, phenol, m-cresol, methylparaben, and propylparaben. Further, the eribulin and/or lenvatinib (or pharmaceutically acceptable salts thereof, such as mesylate salts) formulations optionally include a pharmaceutically acceptable salt, such as sodium chloride at, for example, about physiological concentrations. Thus, in one example, eribulin (or a pharmaceutically acceptable salt thereof, such as eribulin mesylate) is formulated in 0.9% Sodium Chloride Injection (USP). In another example, lenvatinib (or a pharmaceutically acceptable salt thereof, such as lenvatinib mesylate) is formulated for oral administration, e.g., in liquid, tablet, or capsule form.

In some examples, the formulations noted above (and others) can be used for parenteral administration of the drugs. Thus, the drugs can be administered by routes including intravenous, intra-tumoral, peri-tumoral, intra-arterial, intra-dermal, intra-vesical, ophthalmic, intramuscular, intra-dermal, intraperitoneal, pulmonary, subcutaneous, and transcutaneous routes. Other routes can also be used including, for example, transmucosal, transdermal, inhalation, intravaginal, rectal, and oral administration routes.

The dosage of the eribulin and/or lenvatinib (or pharmaceutically acceptable salts thereof, such as mesylate salt) administered may differ markedly depending on the type of target disease, the choice of delivery method, as well as the age, sex, and weight of the patient, the severity of the symptoms, along with other factors, as can be assessed by those of skill in the art. The drugs are administered using amounts and regimens that obtain the desired effect (e.g., tumor regression; see also, e.g., the list of effects (i)-(x) set forth above). The amounts may have additive or synergistic effects on one or more features of cancer treatment (e.g., tumor regression), as is known in the art.

The drugs can be administered to a patient substantially simultaneously or sequentially and in either order (e.g., administration of eribulin (or a pharmaceutically acceptable salt thereof, such as eribulin mesylate) prior to lenvatinib (or a pharmaceutically acceptable salt thereof, such as lenvatinib mesylate), or vice versa). Many regimens used to administer chemotherapeutic drugs involve, for example, administration of a drug (or drugs) followed by repetition of this treatment after a period (e.g., 1-4 weeks) during which the patient recovers from any adverse side effects of the treatment. Typically, the number of cycles of eribulin (or a pharmaceutically acceptable salt thereof, such as eribulin mesylate) and/or lenvatinib (or a pharmaceutically acceptable salt thereof, such as lenvatinib mesylate) administration are 4-8, e.g., 4-7, or 6. It may be desirable to use both drugs at each administration or, alternatively, to have some (or all) of the treatments include only one of the drugs.

Thus, for example, the daily dosage of eribulin (or a pharmaceutically acceptable salt thereof, such as eribulin mesylate) may be in the range of, e.g., 0.001 mg/m$^2$ to about 100 mg/m$^2$ (e.g., in the range of about 0.01 mg/m$^2$ to about 50 mg/m$^2$, 0.1 to about 5 mg/m$^2$, or in the range of about 0.7 mg/m$^2$ to about 1.5 mg/m$^2$, or in any single amount within these ranges (e.g., 1.4 or 1.1 mg/m$^2$)). The drug may be administered as a single dose once a day, week, month, or year, or more than one dose of the drug may be administered per day, week, month, or year. For example, in one administration protocol, the drug may be administered once daily on days 1 and 8 of a 21-day cycle. In another example, the drug may be administered once daily on days 1, 8, and 15 of a 28-day cycle. The drug can be administered over the course of, e.g., 1 minute to 1 hour (or longer), e.g., over 2 to 5 minutes.

More specifically, in one example, a recommended dose of eribulin mesylate is 1.4 mg/m$^2$ administered intravenously over 2 to 5 minutes on days 1 and 8 of a 21-day cycle. A recommended dose of eribulin mesylate in patients with mild hepatic impairment (Child-Pugh A) is 1.1 mg/m$^2$ administered intravenously over 2 to 5 minutes on days 1 and 8 of a 21-day cycle, while a recommended dose of eribulin mesylate in patients with moderate hepatic impairment (Child-Pugh B) is 0.7 mg/m$^2$ administered intravenously over 2 to 5 minutes on days 1 and 8 of a 21-day cycle. Further, a recommended dose of eribulin mesylate in patients with moderate renal impairment (creatinine clearance of 30-50 mL/min) is 1.1 mg/m$^2$ administered intravenously over 2 to 5 minutes on days 1 and 8 of a 21-day cycle. In another example, 1.1 mg/m$^2$ eribulin mesylate is administered intravenously over 2 to 5 minutes on days 1, 8, and 15 of a 28-day cycle.

The daily dosage of lenvatinib (or a pharmaceutically acceptable salt thereof, such as lenvatinib mesylate) for adults is not particularly restricted, although the drug may be administered in the range of, e.g., about 0.1 mg to about 100 mg, e.g., about 4 mg to about 24 mg, or in any single amount within this range (e.g., 15 mg). The drug may be administered as a single dose once a day, week, month, or year, or more than one dose of the drug may be administered per day, week, month, or year. For example, in one administration protocol, the drug may be administered once daily on days 1 and 8 of a 21-day cycle. In other embodiments, the drug may be administered once daily on days 1, 8, and 15 of a 28-day cycle, or on days 1, 8, 15, and 22 of a 35 day cycle. Alternatively, the drug may be administered once daily throughout the course of a cycle of administration of eribulin (or a pharmaceutically acceptable salt thereof, such as eribulin mesylate) and then, optionally, administered daily throughout the course of one or more additional cycles of eribulin (or a pharmaceutically acceptable salt thereof, such as eribulin mesylate) administration. Further, lenvatinib (or a pharmaceutically acceptable salt thereof, such as lenvatinib mesylate) may be administered periodically (e.g., daily, weekly, or twice weekly) following the completion of one or more cycles of eribulin (or a pharmaceutically acceptable salt thereof, such as eribulin mesylate) treatment, optionally, for several additional weeks, months, or years (e.g., indefinitely).

The dosing regimens noted above for eribulin and lenvatinib (or pharmaceutically acceptable salts thereof, such as mesylate salt) typically start on the same "day 1" and different regimens (e.g., any one of those noted above) for the two drugs can be used together. Thus, for example, both drugs may be administered on days 1 and 8 of a 21-day cycle, both drugs may be administered on days 1, 8, and 15 of a 28-day cycle, etc. Alternatively, one drug (e.g., eribulin, or a pharmaceutically acceptable salt thereof, such as eribulin mesylate) may be administered on days 1 and 8 of a 21-day cycle, while the other drug (e.g., lenvatinib, or a pharmaceutically acceptable salt thereof, such as lenvatinib mesylate) may be administered on days 1, 8, and 15 of a 28-day cycle. In a further option, eribulin (or a pharmaceutically acceptable salt thereof, such as eribulin mesylate) is administered intravenously over 2 to 5 minutes on days 1 and 8 of a 21-day cycle, while lenvatinib (or a pharmaceutically acceptable salt thereof, such as lenvatinib mesylate) is administered once daily starting on the same day as eribulin, or a pharmaceutically acceptable salt thereof (e.g., eribulin mesylate) at 4-24 mg.

In addition to eribulin and lenvatinib (or pharmaceutically acceptable salts thereof, such as mesylate salt), the methods of the present invention may also include the administration of one or more additional therapeutic agents. Among these agents, immunomodulatory agents (e.g., antibodies or vaccines), chemotherapeutic/antitumor agents, antibacterial agents, anti-emetics, and anti-inflammatory agents are suitable.

The methods of the invention can be used to treat or prevent cancer in a subject (e.g., a human patient) and/or to decrease tumor size. The subject may be diagnosed with cancer, at risk for developing cancer, in treatment for cancer, or in post-therapy recovery from cancer. Further, the methods can be used to treat or prevent metastases and/or recurrence. The treatment may be chemotherapeutic alone, although treatment in combination with a surgical procedure to remove or reduce the size of a tumor, radiation therapy, and/or ablation therapy is also envisioned.

Types of cancers that can be treated according to the present methods include, for example, breast cancer, pancreatic cancer, lung cancer, colon cancer, rectal cancer, colorectal cancer, ovarian cancer, endometrial cancer, skin cancer (e.g., melanoma), prostate cancer, brain cancer, head and neck cancer, liver cancer, kidney cancer, bladder cancer, gastric cancer, gastrointestinal cancer, cancer of the blood (e.g., leukemia), cancer of the lymphatic system, thyroid cancer, bone cancer (e.g., osteosarcoma), and fibrosarcoma.

Kits

The invention also provides kits that include a container with eribulin (or a pharmaceutically acceptable salt thereof, such as eribulin mesylate) and/or a container with lenvatinib (or a pharmaceutically acceptable salt thereof, such as lenvatinib mesylate). The drugs in such kits can be provided in amounts sufficient to treat cancer in a patient in need thereof (e.g., amounts sufficient for a single administration or for multiple administrations). The kits may thus include multiple containers that each include effective amounts of single-dose eribulin (or a pharmaceutically acceptable salt thereof, such as eribulin mesylate) and/or lenvatinib (or a pharmaceutically acceptable salt thereof, such as lenvatinib mesylate) pharmaceutical composition(s). Optionally, instruments, devices, and/or diluents necessary for administering the pharmaceutical composition(s) may also be included in the kits. Furthermore, the kits may include additional components, such as instructions or administration schedules, for treating a patient with cancer with the drugs.

The present invention is illustrated by the following examples, which are in no way intended to be limiting of the invention.

EXAMPLES

Example 1

Effect of E7389 in Combination with E7080 in A375 Human Malignant Melanoma Xenografts in Mice Summary Antitumor activity of intravenous E7389 (eribulin mesylate) in combination with oral E7080 (lenvatinib mesylate) was examined in a preclinical model with subcutaneous A375 human malignant melanoma xenografts in female athymic mice. E7389 was administered at 0.05, 0.2, or 3.0 mg/kg (maximum tolerable dose [MTD]) alone, or was co-administered with 15 mg/kg E7080 (MTD). The combination of E7389 and E7080 generated tumor regression, while each single agent resulted in tumor growth delay. Administration of 3.0 mg/kg E7389 on a once per week for two weeks (Q7Dx2) schedule in combination with 15 mg/kg E7080 daily dosing for 14 days (Q1Dx14) resulted in additional body weight loss in animals. However, body weight recovered upon completion of drug treatment.

Methods

Preparation of Test Compound Dosing Formulations

E7080 was dissolved in WFI at a concentration of 1.5 mg/m L. E7080 dosing solution was formulated for 7 days. The stock solution was aliquoted and stored at 4° C. until use. 0.5 mg/mL E7389 was diluted with 3% ETOH in saline at concentrations of 0.005, 0.02, and 0.3 mg/m L. E7389 was freshly formulated for each day of dosing.

Measurement of Antitumor Activity

A375 human malignant melanoma cells were maintained in monolayer cultures in Dulbecco's Modified Eagle's Medium (DMEM) growth medium supplemented with 10% Fetal Bovine Serum and 1% of Penicillin-Streptomycin-Glutamine at 37° C. in a 5% $CO_2$ humidified incubator. On the day of inoculation, cells were harvested by Trypsinization, washed, and mixed 1:1 (v/v) with ice-cold Phosphate Buffered Saline (PBS)/Matrigel. A375 malignant melanoma cells ($5\times10^6$ cells per animal) were inoculated subcutaneously near the right axillary area using a 26-gauge needle in a 0.1 mL volume in 80 female immuncompromised mice (Mouse/Crl:NU-Foxn1$^{nu}$; Charles River Laboratories).

The experiment consisted of a vehicle-treated control group, a single agent drug-treated group for either E7389 or E7080, and three combination drug-treated groups (summarized in Table 1). Each group was composed of six mice for a total of 48 mice on the first day of treatment. Forty eight out of 80 mice were selected based on their tumor volumes, and randomly divided into eight groups which resulted in approximately 300 mm$^3$ of mean tumor volume in each group 17 days after tumor implantation. Following randomization, drug treatment was initiated. E7080 was orally administered daily for 14 days (Q1Dx14) at a volume of 0.1 mL per 10 g body weight. E7389 (0.05 mg/kg) was intravenously administered daily for 14 days. In the combination group, E7389 was administered three hours after oral administration of E7080. E7389 at 0.2 or 3.0 mg/kg was administered Q7Dx2 either as a single agent or in combination with E7080 (Q1Dx14). The control group was treated with vehicle (WFI for oral daily dosing (Q1Dx14) for 14 days and 3% ETOH in saline for intravenous dosing, on a Q7Dx2 schedule).

The general health of the mice was monitored daily. Tumor volume was determined by caliper measurements (mm) using the formula $(l\times w^2)/2 = mm^3$, where l and w refer to the larger and smaller perpendicular dimensions collected at each measurement. Tumor dimensions and body weight were recorded twice per week starting the first day of treatment. Relative body weight was calculated as follows: Relative body weight=(body weight on day of measurement)/(body weight on first day of treatment).

The data generated consisted of group mean body weights at each measurement and group mean tumor volumes at each measurement. The mean±SEM for tumor volume and relative body weight for each experimental group was calculated.

Animals whose tumor measurements reached 20 mm at the longest axis, or in which ulceration occurred, were euthanized prior to study termination. The study was terminated on day 30.

Results

Figure 1:
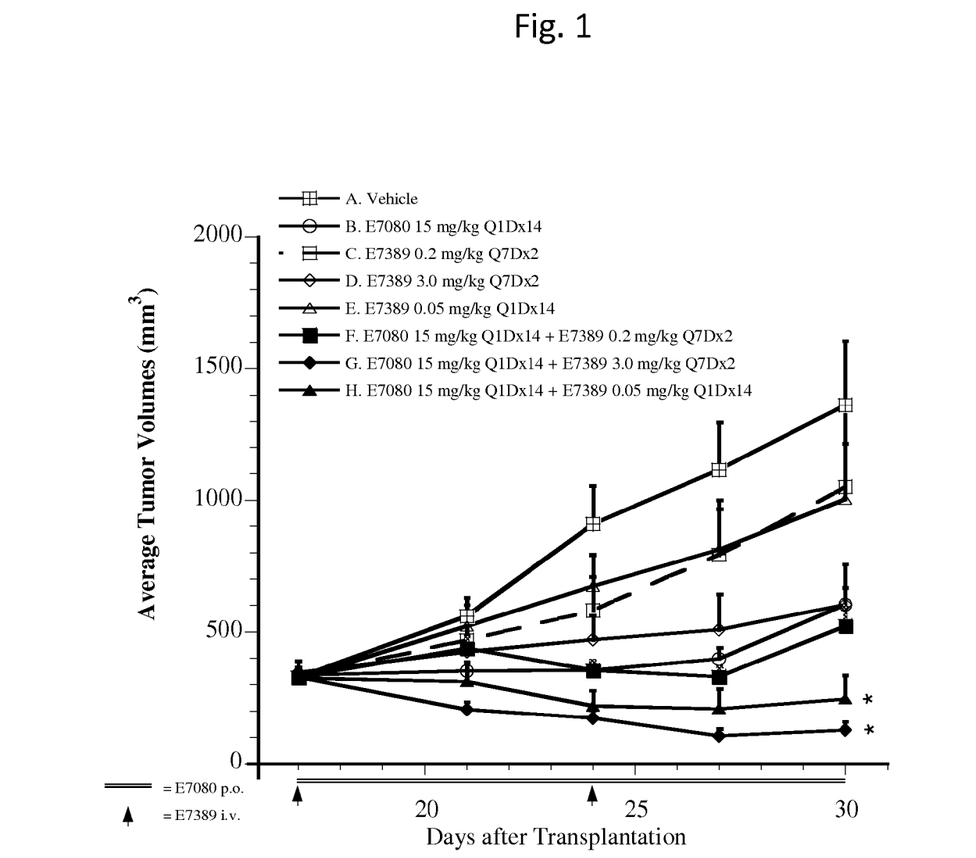
FIG. 1 is a graph showing the antitumor effects of E7389 in combination with E7080 in an A375 human malignant melanoma xenograft model in mice. Data represent the mean±SEM (n=6). Arrows on 17 and 24 days after transplantation show starting day of treatments, the arrow represents E7389, and the line represents E7080. i.v.=intravenous, p.o.=per os, Q1Dx14=once daily for 14 days, Q7Dx2=once a week for 2 weeks. *P<0.05 versus E7389 3.0 mg/kg single agent on day 30 (one-way analysis of variance followed by the Dunnett's multiple comparison test).
Figure 2:
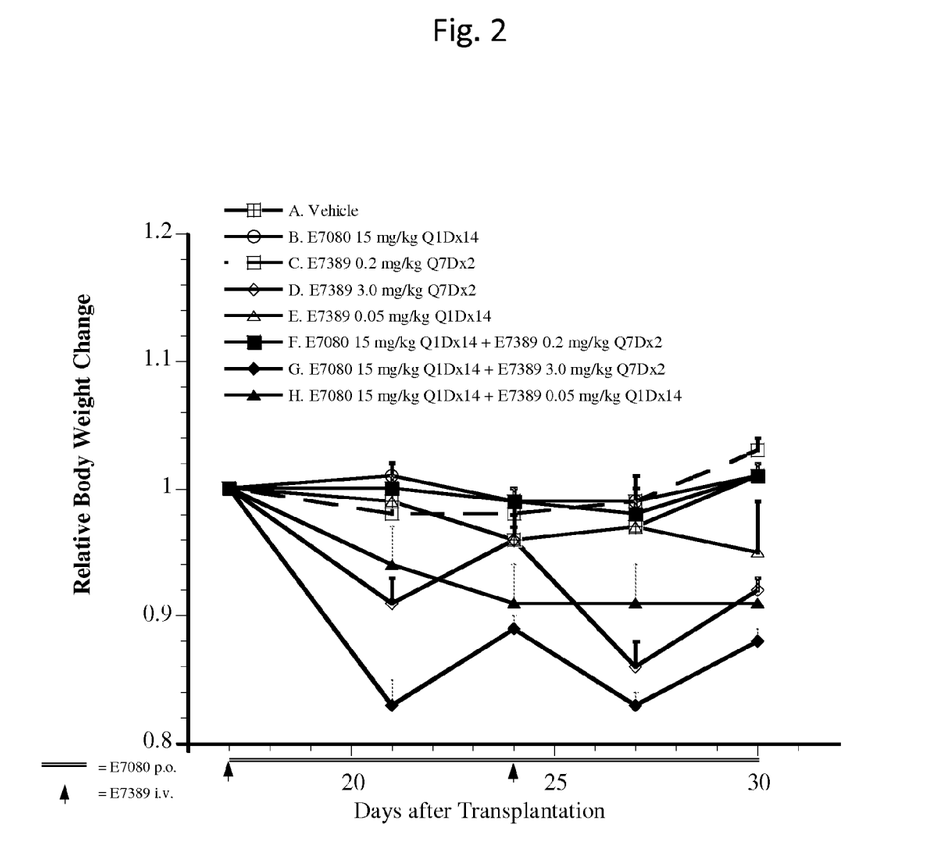
FIG. 2 is a graph showing relative body weight change of animals treated with E7389 alone, E7080 alone, and E7389+ E7080 in combination. Data represent the mean±SEM (n=6). Arrows on 17 and 24 days after transplantation show starting day of treatments, the arrow represents E7389, and the line represents E7080. i.v.=intravenous, p.o.=per os, Q1Dx14=once daily for 14 days, Q7Dx2=once a week for 2 weeks. Body weight loss was observed after E7389 administered alone at 3.0 mg/kg and in the combination treatment groups. Partial recovery from body weight loss was observed in all mice upon completion of drug treatment.

FIG. 1 shows the effect of E7389 in combination with E7080 in A375 human malignant melanoma xenografts in mice. Single agent administration of either E7389 or E7080 at the highest dose of 3.0 mg/kg (MTD for E7389) and 15 mg/kg (MTD for E7080) resulted in tumor growth delay, but not tumor regression. The combination of E7389 with E7080 potentiated the antitumor activity of E7389 at all doses tested. Tumor growth inhibition was observed at all combination groups in a dose-dependent fashion (FIG. 1). Administration of 3.0 mg/kg E7389 in combination with E7080 caused additional body weight loss. However, recovery from body weight loss was observed upon completion of drug treatment (FIG. 2).

E7080 was administered orally once daily for 14 days. E7389 at 0.05 mg/kg was intravenously administered daily for 14 days. In the combination setting, E7389 was dosed three hours after the oral administration of E7080. E7389 at 0.2 or 3.0 mg/kg was administered at Q7Dx2 either as a single agent or in combination. The study was terminated on 30 days after transplantation. Administration of 3.0 mg/kg (Q7Dx2) and 0.05 mg/kg E7389 (Q1Dx14) combined with 15 mg/kg E7080 daily administration (Q1Dx14) resulted in tumor regression in this study.

Conclusions

E7389 alone at 3.0 mg/kg and combination treatment showed strong antitumor activity in the A375 human malignant melanoma xenograft model. Body weight loss appeared reversible as all animals partially recovered upon completion of drug treatment. E7389 administered at a low dose on a metronomic schedule (0.05 mg/kg Q1Dx14) combined with 15 mg/kg E7080 daily dosing (Q1Dx14) resulted in significant tumor regression compared to E7389 3.0 mg/kg single agent treatment.

Example 2

Treatment of Breast Cancer in a Patient by Combination Therapy

A patient with breast cancer is treated with a combination of E7389 (eribulin mesylate) and E7080 (lenvatinib mesylate) according to the following protocol. E7389 is administered at 1.4 mg/m$^2$ intravenously over 2 to 5 minutes on

TABLE 1

Study Design for Investigation of Antitumor activity of E7389 in combination with E7080 in A375 human malignant melanoma xenografts

| Group | Treatment | No. of animals |
|---|---|---|
| A | Vehicle (WFI) p.o. Q1Dx14 + 3% ETOH saline i.v. Q7Dx2 | 6 |
| B | E7080 15 mg/kg p.o. Q1Dx14 | 6 |
| C | E7389 0.2 mg/kg i.v. Q7Dx2 | 6 |
| D | E7389 3.0 mg/kg i.v. Q7Dx2 | 6 |
| E | E7389 0.05 mg/kg i.v. Q1Dx14 | 6 |
| F | E7080 15 mg/kg p.o. Q1Dx14 + E7389 0.2 mg/kg i.v. Q7Dx2 | 6 |
| G | E7080 15 mg/kg p.o. Q1Dx14 + E7389 3.0 mg/kg i.v. Q7Dx2 | 6 |
| H | E7080 15 mg/kg p.o. Q1Dx14 + E7389 0.05 mg/kg i.v. Q1Dx14 | 6 |

Statistical Analysis

Statistical analysis of the E7389 3.0 mg/kg single agent administration and combination with E7080 15 mg/kg groups was performed by a one-way analysis of variance (ANOVA) followed by Dunnett's multiple comparison test. A value of P<0.05 was considered statistically significant. The statistical analysis was performed using Graphpad prism software (version 5).

days 1 and 8 of a 21-day cycle. E7080 is orally administered at 24 mg/day on each day of the 21-day cycle of E7389 treatment, starting on the same day. The patient is treated for a total of 4-6 cycles, depending upon factors such as the occurrence and severity of side effects, as well as clinical effects, as determined by a medical professional. Optionally, E7080 treatment continues after the end of the E7389 treatment cycles.

Example 3

Effect of E7389 in Combination with E7080 in NCI-H1993 and PC-9 Human Non-Small Cell Lung Cancer Xenografts in Mice Summary Antitumor activity of intravenous E7389 (eribulin mesylate) in combination with oral E7080 (lenvatinib mesylate) was examined in a preclinical model with subcutaneous NCI-H1993 or PC-9 human non-small cell lung cancer xenografts in female athymic mice. E7389 was administered at 1.5 mg/kg alone, or was co-administered with 10 mg/kg E7080. The combination of E7389 and E7080 showed significantly strong antitumor activity than that of each monotherapy.

Methods

Preparation of Test Compound Dosing Formulations

E7080 was dissolved in DW at a concentration of 1.0 mg/mL. 0.5 mg/mL E7389 was diluted with saline at concentrations of 0.15 mg/m L.

Measurement of Antitumor Activity

Human non-small cell lung cancer cell lines, NCI-H1993 and PC-9, were maintained in monolayer cultures in RPMI-1640 medium supplemented with 10% Fetal Bovine Serum and 1% of Penicillin-Streptomycin-Amphotericin at 37° C. in a 5% $CO_2$ humidified incubator. On the day of inoculation, cells were harvested by Trypsinization, washed, and mixed 1:1 (v/v) with medium/GelTrex. NCI-H1993 and PC-9 human non-small cell lung cancer cells ($10 \times 10^6$ cells per animal) were inoculated subcutaneously near the right axillary area using a 26-gauge needle in a 0.1 mL volume in female immuncompromised mice (Mouse: BALB/c Slc nu/nu; Japan SLC, Inc.).

The experiment consisted of a no inject control group, a single agent drug-treated group for either E7389 (1.5 mg/kg) or E7080 (10 mg/kg), and combination drug-treated groups. Each group was composed of five mice. Mice were selected based on their tumor volumes, and randomly divided into groups which resulted in approximately 200 mm$^3$ (NCI-H1993: 191 mm$^3$, PC-9: 227 mm$^3$) of mean tumor volume in each group 10 days (NCI-H1993) or 8 days (PC-9) after tumor cells inoculation. Following randomization, drug treatment was initiated. E7389 (1.5 mg/kg) was intravenously administered weekly for two weeks (Q7Dx2). E7080 was orally administered daily for 12 days (Q1Dx12). Both drugs were administered at a volume of 0.1 mL per 10 g body weight.

Tumor volume was determined by caliper measurements (mm) using the formula

Tumor volume (mm$^3$)=length (mm)×width$^2$(mm$^2$)×½

Length: largest diameter of tumor

Width: diameter perpendicular to length

The mean±SD for tumor volume for each experimental group was calculated.

Statistical Analysis

Statistical analysis of each single agent administration group and combination group or no inject group was performed by a two-way RM-ANOVA test. A value of $P<0.05$ was considered statistically significant. The statistical analysis was performed using Graphpad prism software (version 6.02).

Results

Figure 3:
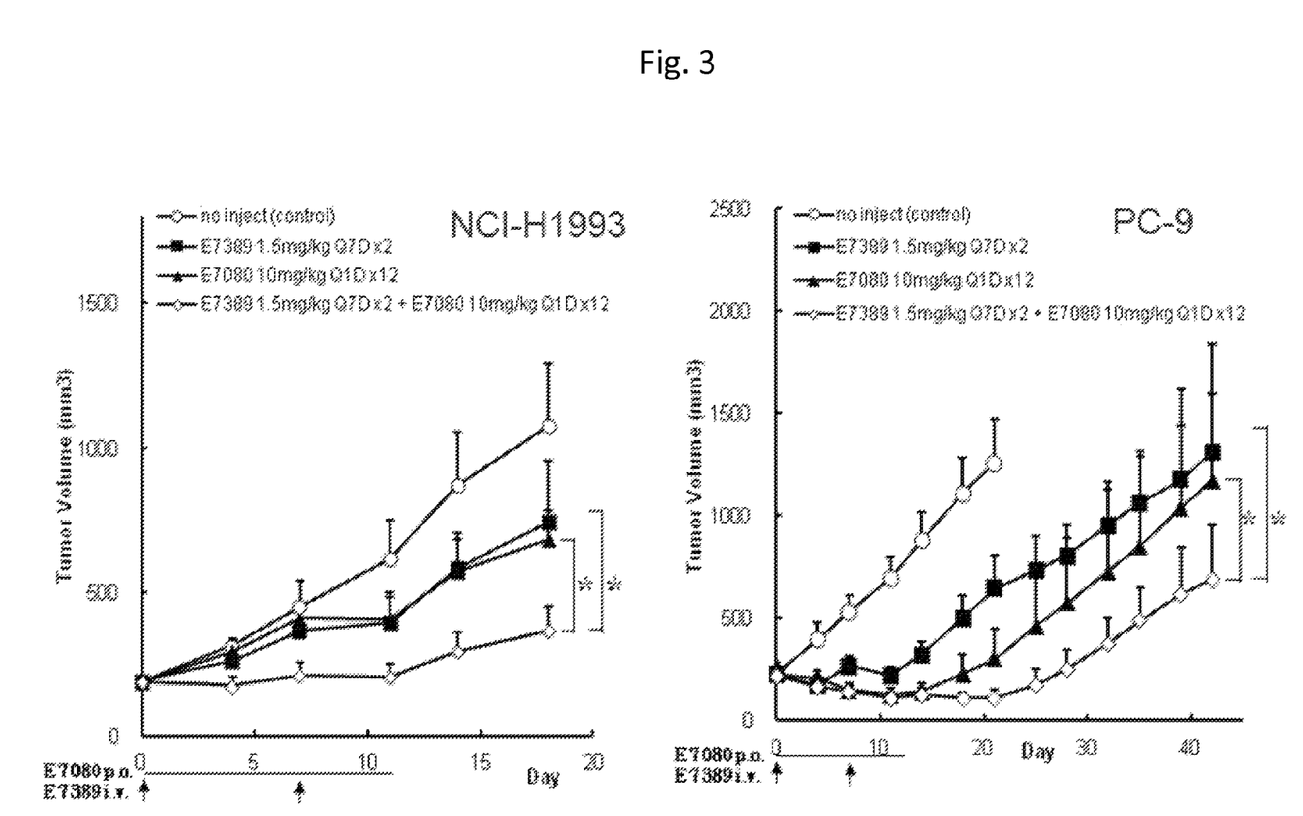
FIG. 3 is a graph showing the antitumor effects of E7389 in combination with E7080 in NCI-H1993 (left) or PC-9 (right) human non-small cell lung cancer xenografts in mice. Data represent the mean±SD (n=5). The arrows on Day 0 and Day 7 show injection of E7389, and the line from Day 0 to Day 11 show treatment of E7080. i.v.=intravenous, p.o.=per os, Q1Dx12=once daily for 12 days, Q7Dx2=once a week for 2 weeks. *P<0.05: statically analysis of combination group vs. each single therapy group (repeated measured ANOVA test).

FIG. 3 shows the effect of E7389 in combination with E7080 in NCI-H1993 (left) or PC-9 (right) human non-small cell lung cancer xenografts in mice. Single treatment of E7389 (1.5 mg/kg) or E7080 (10 mg/kg) resulted significant antitumor activity in both xenograft models. The combination of E7389 with E7080 significantly potentiated the antitumor activity than that of each single treatment in both xenograft models.

Conclusions

Combination treatment of E7389 and E7080 showed significantly stronger antitumor activity than that of each single treatment.

Specific Embodiments

Specific embodiments of the invention are as follows:

[1] A method for treating a subject having or at risk of developing cancer, the method comprising administering to the subject (i) eribulin or a pharmaceutically acceptable salt thereof, and (ii) lenvatinib or a pharmaceutically acceptable salt thereof.

[2] The method of [1], wherein said subject is a human patient.

[3] The method of [1] or [2], wherein said subject is diagnosed with cancer, in treatment for cancer, or in post-therapy recovery from cancer.

[4] The method of any one of [1] to [3], wherein said cancer is a primary tumor.

[5] The method of any one of [1] to [3], wherein said cancer is a metastasis.

[6] The method of any one of [1] to [5], wherein said cancer is a solid tumor.

[7] The method of any one of [1] to [6], wherein said cancer is selected from the group consisting of breast cancer, pancreatic cancer, lung cancer, colon cancer, rectal cancer, colorectal cancer, ovarian cancer, endometrial cancer, skin cancer (e.g., melanoma), prostate cancer, brain cancer, head and neck cancer, liver cancer, kidney cancer, bladder cancer, gastric cancer, gastrointestinal cancer, cancer of the blood (e.g., leukemia), cancer of the lymphatic system, thyroid cancer, bone cancer (e.g., osteosarcoma), and fibrosarcoma.

[8] The method of any one of [1] to [7], wherein said eribulin or said pharmaceutically acceptable salt thereof is eribulin mesylate.

[9] The method of any one of [1] to [8], wherein said lenvatinib or said pharmaceutically acceptable salt thereof is lenvatinib mesylate.

[10] The method of any one of [1] to [9], wherein said eribulin or said pharmaceutically acceptable salt thereof is administered by intravenous infusion.

[11] The method of [10], wherein said intravenous infusion is for about 1 to about 20 minutes.

[12] The method of [11], wherein said intravenous infusion is for about 2 to about 5 minutes.

[13] The method of any one of [1] to [12], wherein said eribulin or said pharmaceutically acceptable salt thereof is administered in an amount in the range of about 0.1 mg/m$^2$ to about 20 mg/m$^2$.

[14] The method of [13], wherein said eribulin or said pharmaceutically acceptable salt thereof is administered in an amount of about 1.4 mg/m$^2$ or 1.1 mg/m$^2$.

[15] The method of any one of [1] to [14], wherein said eribulin or said pharmaceutically acceptable salt thereof is administered once on each of days 1 and 8 of a 21-day cycle.

[16] The method of any one of [1] to [15], wherein said lenvatinib, or said pharmaceutically acceptable salt thereof, is administered orally.

[17] The method of any one of [1] to [16], wherein said lenvatinib, or said pharmaceutically acceptable salt thereof, is administered in an amount in the range of about 0.1 mg to about 100 mg.

[18] The method of [17], wherein said lenvatinib, or said pharmaceutically acceptable salt thereof, is administered in an amount in the range of about 4 mg to about 24 mg.

[19] The method of any one of [1] to [18], wherein said lenvatinib, or said pharmaceutically acceptable salt thereof, is administered daily.

[20] The method of any one of [1] to [19], wherein said eribulin or said pharmaceutically acceptable salt thereof, and said lenvatinib, or said pharmaceutically acceptable salt thereof, are administered substantially simultaneously or sequentially.

[21] The method of any one of [1] to [20], wherein said treating: (i) reduces the number of cancer cells; (ii) reduces tumor volume; (iii) increases tumor regression rate; (iv) reduces or slows cancer cell infiltration into peripheral organs; (v) reduces or slows tumor metastasis; (vi) reduces or inhibits tumor growth; (vii) prevents or delays occurrence and/or recurrence of the cancer and/or extends disease- or tumor-free survival time; (viii) increases overall survival time; (ix) reduces the frequency of treatment; and/or (x) relieves one or more of symptoms associated with the cancer.

[22] A method for decreasing the size of a tumor in a subject, the method comprising administering to the subject (i) eribulin or a pharmaceutically acceptable salt thereof, and (ii) lenvatinib or a pharmaceutically acceptable salt thereof.

[23] A kit for use in treating cancer, decreasing tumor size, or inducing or increasing an immune response to a tumor in a subject, the kit comprising (i) eribulin or a pharmaceutically acceptable salt thereof, and (ii) lenvatinib or a pharmaceutically acceptable salt thereof.

[24] The kit of [23], wherein said (i) eribulin or said pharmaceutically acceptable salt thereof, and said (ii) lenvatinib or said pharmaceutically acceptable salt thereof, are in dosage form.

[25] Eribulin or a pharmaceutically acceptable salt thereof for use in a method for treating a subject having or at risk of developing cancer, characterized in that said compound is administered to the subject with lenvatinib or a pharmaceutically acceptable salt thereof.

[26] The eribulin or the pharmaceutically acceptable salt thereof of [25], wherein said compound and said lenvatinib, or said pharmaceutically acceptable salt thereof, are administered substantially simultaneously or sequentially.

[27] The eribulin or the pharmaceutically acceptable salt thereof of [25] or [26], wherein said compound is eribulin mesylate.

[28] Lenvatinib or a pharmaceutically acceptable salt thereof for use in a method for treating a subject having or at risk of developing cancer, characterized in that said compound is administered to the subject with eribulin or a pharmaceutically acceptable salt thereof.

[29] The lenvatinib or the pharmaceutically acceptable salt thereof of [28], wherein said compound and said eribulin, or said pharmaceutically acceptable salt thereof, are administered substantially simultaneously or sequentially.

[30] The lenvatinib or the pharmaceutically acceptable salt thereof of [28] or [29], wherein said compound is lenvatinib mesylate.

[31] A pharmaceutical composition for treating a subject having or at risk of developing cancer comprising eribulin or a pharmaceutically acceptable salt thereof, characterized in that said pharmaceutical composition is administered to a subject with lenvatinib or a pharmaceutically acceptable salt thereof.

[32] A pharmaceutical composition for treating a subject having or at risk of developing cancer comprising lenvatinib or a pharmaceutically acceptable salt thereof, characterized in that said pharmaceutical composition is administered to a subject with eribulin or a pharmaceutically acceptable salt thereof.

[33] The pharmaceutical composition of [31] or [32], wherein said eribulin or said pharmaceutically acceptable salt thereof, and said lenvatinib, or said pharmaceutically acceptable salt thereof, are administered substantially simultaneously or sequentially.

[34] The pharmaceutical composition of any one of [31] to [33], wherein said eribulin or said pharmaceutically acceptable salt thereof is eribulin mesylate.

[35] The pharmaceutical composition of any one of [31] to [33], wherein said lenvatinib or said pharmaceutically acceptable salt thereof is lenvatinib mesylate.

[36]. Use of (i) eribulin or a pharmaceutically acceptable salt thereof, and (ii) lenvatinib or a pharmaceutically acceptable salt thereof, in the treatment of a subject having or at risk of developing cancer, or for decreasing the size of a tumor in a subject.

[37]. Use of (i) eribulin or a pharmaceutically acceptable salt thereof, and (ii) lenvatinib or a pharmaceutically acceptable salt thereof, in the preparation of a medicament for use in the treatment of a subject having or at risk of developing cancer, or for decreasing the size of a tumor in a subject.

The various embodiments noted above with respect to items [2] to [21] (methods) are applicable to items [36] and [37] (uses).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety.

Use of singular forms herein, such as "a" and "the," does not exclude indication of the corresponding plural form, unless the context indicates to the contrary. Similarly, use of plural terms does not exclude indication of a corresponding singular form. Other embodiments are within the scope of the following claims.

What is claimed is:

1. A method for treating a subject having or at risk of developing cancer, the method comprising administering to the subject in a cancer treatment regimen (i) eribulin or a pharmaceutically acceptable salt thereof, and (ii) lenvatinib or a pharmaceutically acceptable salt thereof, wherein said cancer is selected from the group consisting of breast cancer, pancreatic cancer, lung cancer, colon cancer, rectal cancer, colorectal cancer, ovarian cancer, endometrial cancer, skin cancer, prostate cancer, brain cancer, head and neck cancer, liver cancer, kidney cancer, bladder cancer, gastric cancer, gastrointestinal cancer, cancer of the blood, cancer of the lymphatic system, thyroid cancer, bone cancer, and fibrosarcoma.

2. The method of claim 1, wherein said subject is a human patient.

3. The method of claim 1, wherein said subject is diagnosed with cancer, in treatment for cancer, or in post-therapy recovery from cancer.

4. The method of claim 1, wherein said cancer is a primary tumor or a metastasis.

5. The method of claim 1, wherein said cancer is a solid tumor.

6. The method of claim 1, wherein said skin cancer is melanoma.

7. The method of claim 1, wherein said eribulin or said pharmaceutically acceptable salt thereof is eribulin mesylate.

8. The method of claim 1, wherein said lenvatinib or said pharmaceutically acceptable salt thereof is lenvatinib mesylate.

9. The method of claim 1, wherein said eribulin or said pharmaceutically acceptable salt thereof is administered by intravenous infusion.

10. The method of claim 9, wherein said intravenous infusion is for about 1 to about 20 minutes.

11. The method of claim 10, wherein said intravenous infusion is for about 2 to about 5 minutes.

12. The method of claim 1, wherein said eribulin or said pharmaceutically acceptable salt thereof is administered in an amount in the range of about 0.1 mg/m$^2$ to about 20 mg/m$^2$, or about 1.4 mg/m$^2$ or 1.1 mg/m$^2$.

13. The method of claim 1, wherein said eribulin or said pharmaceutically acceptable salt thereof is administered once on each of days 1 and 8 of a 21-day cycle.

14. The method of claim 1, wherein said lenvatinib, or said pharmaceutically acceptable salt thereof, is administered daily.

15. The method of claim 1, wherein said lenvatinib, or said pharmaceutically acceptable salt thereof, is administered orally.

16. The method of claim 1, wherein said eribulin or said pharmaceutically acceptable salt thereof, and said lenvatinib, or said pharmaceutically acceptable salt thereof, are administered substantially simultaneously.

17. The method of claim 1, wherein said cancer of the blood is leukemia.

18. The method of claim 1, wherein said bone cancer is osteosarcoma.

19. The method of claim 1, wherein said cancer is breast cancer.

20. The method of claim 1, wherein said cancer is lung cancer.

21. The method of claim 20, wherein said lung cancer is non-small cell lung cancer.

22. The method of claim 1, wherein said lenvatinib, or said pharmaceutically acceptable salt thereof, is administered in an amount in the range of about 0.1 mg to about 100 mg.

23. The method of claim 22, wherein said lenvatinib, or said pharmaceutically acceptable salt thereof, is administered in an amount in the range of about 4 mg to about 24 mg.

24. The method of claim 1, wherein said eribulin or said pharmaceutically acceptable salt thereof, and said lenvatinib, or said pharmaceutically acceptable salt thereof, are administered sequentially.

25. The method of claim 1, wherein said eribulin or said pharmaceutically acceptable salt thereof is administered once on each of days 1 and 8 of a 21-day cycle, and said lenvatinib, or said pharmaceutically acceptable salt thereof, is administered daily.

* * * * *

UNITED STATES PATENT AND TRADEMARK OFFICE
CERTIFICATE OF CORRECTION

PATENT NO. : 9,549,922 B2
APPLICATION NO. : 14/315930
DATED : January 24, 2017
INVENTOR(S) : Kenichi Nomoto et al.

Page 1 of 1

It is certified that error appears in the above-identified patent and that said Letters Patent is hereby corrected as shown below:

In the Specification

Column 5, Line 7, replace "methansulfonic" with --methanesulfonic--.

Column 8, Line 56, replace "mg/m L" with --mg/mL--.

Column 9, Line 5, replace "immuncompromised" with --immunocompromised--;

Line 41, replace "reached 20 mm" with --reached $\geq$20 mm--.

Column 11, Line 21, replace "mg/m L" with --mg/mL--;

Line 33, replace "immuncompromised" with --immunocompromised--.

Signed and Sealed this
Ninth Day of May, 2017

Michelle K. Lee
*Director of the United States Patent and Trademark Office*